United States Patent [19]

Johnson

[11] Patent Number: 4,462,395
[45] Date of Patent: Jul. 31, 1984

[54] ARTHROSCOPIC LIGAMENTOUS AND CAPSULAR FIXATION SYSTEM

[76] Inventor: Lanny L. Johnson, 3800 S. Hagadorn Rd., Okemos, Mich. 48864

[21] Appl. No.: 471,336

[22] Filed: Mar. 2, 1983

[51] Int. Cl.³ .............................................. A61F 5/04
[52] U.S. Cl. .............................. 128/92 B; 128/92 EC
[58] Field of Search .............. 128/92 B, 92 R, 92 EC, 128/92 BA, 334 R, 334 C

[56] References Cited

U.S. PATENT DOCUMENTS

| | | | |
|---|---|---|---|
| 3,208,450 | 9/1965 | Abelson | 128/92 EC |
| 3,626,935 | 12/1971 | Pollock et al. | 128/92 EC |
| 3,875,936 | 4/1975 | Volz | 128/92 B |
| 4,153,053 | 5/1979 | Figallo | 128/92 EC X |

OTHER PUBLICATIONS

1983 Catalog of Howmedica, Inc., pp. 22 and G-27.
1983 Catalog of Richards Medical Supply Co., pp. 72-74.

*Primary Examiner*—John D. Yasko
*Attorney, Agent, or Firm*—Cushman, Darby & Cushman

[57] ABSTRACT

A fixation system for arthroscopic surgical procedures is disclosed. A staple is adapted to be removably secured to the end of an elongated impact-type driver-extractor device. The staple and the end of the driver-extractor are dimensioned to be received within a cylindrical cannula which guides the staple to its point of affixation within the patient's body. Actuation of the driver-extractor permits the staple to be hammered into place. By a reversal in this procedure, a previously implanted staple can be removed from the patient.

10 Claims, 7 Drawing Figures

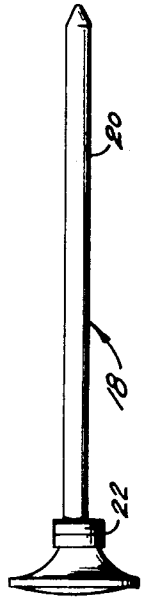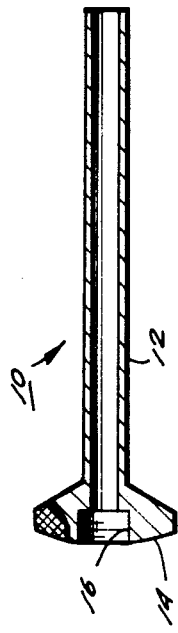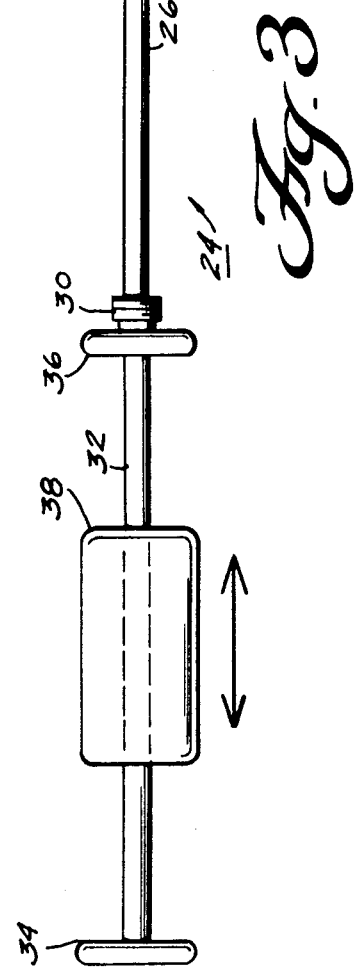

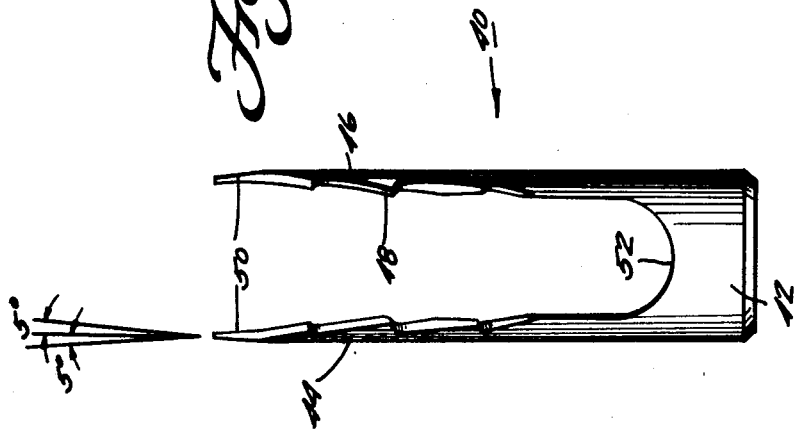
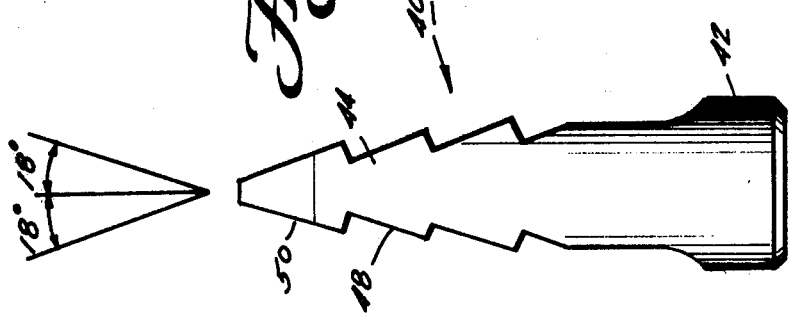
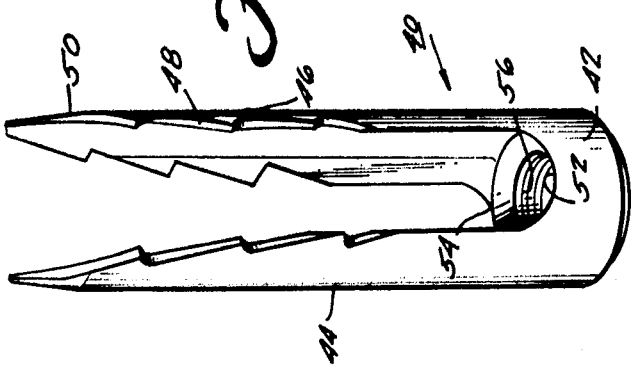
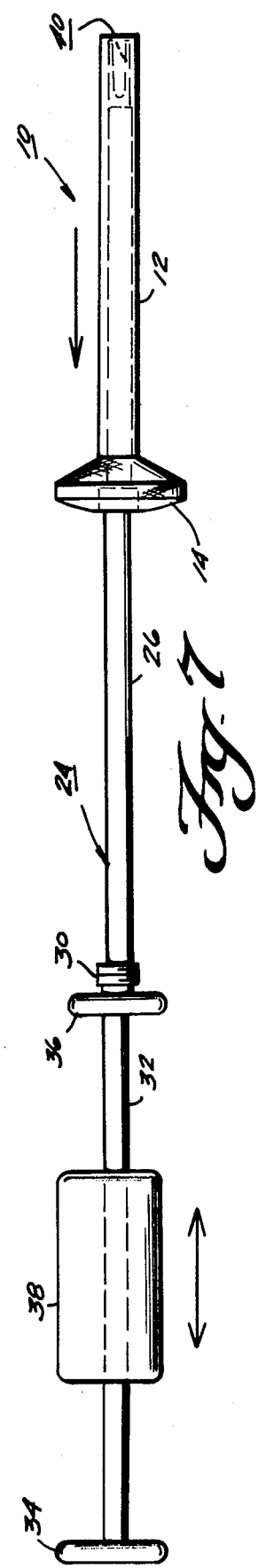

ARTHROSCOPIC LIGAMENTOUS AND CAPSULAR FIXATION SYSTEM

BACKGROUND OF THE INVENTION

An important advance in the field of orthopedics has been the development of arthroscopic surgical techniques. Instead of conventionally opening the area being operated upon, arthroscopy is accomplished merely by providing a small number of punctures—typically three—through which specially designed instruments are inserted to permit the observation and repair of the damaged parts.

One procedure which is difficult with conventional open surgical methods, and virtually impossible to accomplish by arthroscopic techniques, is the suturing of torn anterior cruciate ligaments in the knee. Consequently, the usual correction of such a condition requires complicated open surgery knee joint or capsular repairs, sometimes involving the grafting of tendons or the use of fibers of plastic or carbon materials.

SUMMARY OF THE INVENTION

The present invention permits the repair of anterior cruciate ligaments by arthroscopic techniques. More particularly, a staple fixation system is provided which secures the anterior cruciate pedicle to the femur. This type of system also is suitable for arthroscopically repairing other ligaments or torn capsular tissues in the knee or shoulder joints. For example, instead of a conventional open surgical procedure requiring an hour or more, and which may even necessitate a blood transfusion, a dislocated shoulder can be repaired in a half hour by an arthroscopic stapling procedure utilizing only three punctures. Since the patient's discomfort is dramatically reduced, such a procedure often can be performed on an outpatient basis. Furthermore, recovery is hastened due to decreased tissue disruption.

Briefly, the invention utilizes a staple which has a circular cross-section and which is adapted to be removably secured to the end of an elongated impact-type driver-extractor device. The staple, and the end of the driver-extractor to which the staple is secured, are dimensioned to be received with a cylindrical cannula which passes through one of the punctures in the patient to guide the staple to its point of affixation. Actuation of the driver-extractor permits the staple either to be hammered into place or to be removed from its anchorage in the patient's bone.

The invention now will be described in greater detail with respect to the accompanying drawings, wherein:

FIG. 1 is a longitudinal cross-sectional view of the cannula portion of the present invention;

FIG. 2 is a side elevational view of a trocar device for facilitating the positioning of the cannula within a patient;

FIG. 3 is a side elevational view of the driver-extractor portion of the invention;

FIG. 4 is a perspective view of a preferred embodiment of the staple portion of the invention;

FIG. 5 is a side elevational view of the staple shown in FIG. 4;

FIG. 6 is a side elevational view of the staple shown in FIG. 4 but taken at an angle of 90° from the side shown in FIG. 5; and FIG. 7 illustrates the various portions of the invention in their operative relationship with respect to one another.

DETAILED DESCRIPTION OF THE INVENTION

Referring to the drawings, FIG. 1 illustrates the cannula portion of the invention which serves as a guide for the initial positioning and the removal of a surgical staple. More particularly, the cannula 10 comprises a hollow cylindrical portion 12 provided with a knurled knob 14 at one end thereof, The knob is provided with an interiorly threaded passage 16 which is axially aligned with the longitudinal axis of cylindrical portion 12.

To facilitate the entry of the cannula into a punctured opening in the patient and through the tissue to the area being repaired, a trocar is provided. This device 18 is detailed in FIG. 2 and comprises a pointed cylindrical portion 20 having an outer diameter slightly less than the inner diameter of the hollowed cylindrical portion 12 of the cannula 10. A threaded boss 22 is provided at one end of the trocar, and a knob 24 is secured to the opposite side of the boss 22 from cylindrical portion 20.

The cannula and trocar are joined in operative relationship by inserting portion 20 of the trocar within the cylindrical portion 12 of the cannula and using knob 24 to screw boss 22 within the cannula's threaded aperture 16. The cylindrical portion 20 of the trocar is dimensioned such that with the cannula and trocar united, the pointed end of portion 20 extends beyond the end of the cannula's cylindrical portion 12. Consequently, when inserting the unit into the patient, the pointed end minimizes disruption of the tissue, and tissue is prevented from entering portion 12 of the cannula.

After the cannula is properly positioned, the trocar is unscrewed and removed from the cannula so as to permit a staple to be guided to its point of affixation. More particularly, FIG. 3 illustrates a driver-extractor device 24 comprising a first cylindrical portion 26 having an outer diameter slightly less than the inner diameter of the cannula's hollowed cylindrical portion 12. Portion 26 is substantially longer than portion 12 for reasons hereinafter to be described. A threaded projection 28 is located at one end of portion 26, and at the opposite end thereof, a threaded boss 30 is provided. A second cylindrical portion 32 is axially aligned with portion 26 on the opposite side of boss 30 from portion 26. A pair of annular stop elements 34 and 36 are secured to the opposite ends of cylindrical portion 32, and a movable member 38 of relatively substantial mass is arranged to slide along portion 32 between the stop members.

The surgical staple which is secured to the threaded projection 28 of the driver-extractor is illustrated in FIGS. 4–6. More particularly, the staple 40 comprises a cylindrical base 42 from which a pair of tapered legs 44 and 46 project, the legs having outer surfaces generally corresponding to the curvature of base 42. The legs are serrated along their edges to form a series of teeth 48. Each tooth is inclined at an angle of approximately 18° to the longitudinal axis of the staple. The legs terminate at square-ended tips 50, the inner and outer surfaces of which are sloped at an angle of about 5° to the longitudinal axis of its respective leg. The formation of the tips in this manner prevents the spreading or collapsing of the legs when they are driven into bone, while the arrangement of the teeth which has been described provides strong fixation between the staple and bone without presenting difficulties in removing the staple.

The legs 44 and 46 meet base 42 at generally U-shaped intersections 52 and 54. Such a configuration accommodates the tissue being secured to the bone by the staple and prevents the tissue from being cut.

The base 42 of the staple is provided with a threaded aperture 56 for receiving the projection 28 of the driver-extractor.

The operation of the system now will be explained with reference to FIG. 7. After the cannula 10 has been properly positioned and the trocar removed in the manner previously described, a staple 40 is secured to the projection 28 of driver-extractor 24. The staple and portion 26 of the driver-extractor then are inserted within the hollowed cylindrical portion 12 of the cannula. The cannula lends stability to the staple until it is properly positioned at the location where it is to be driven into the bone to secure ligamentous or capsular tissue. The cannula then is withdrawn along portion 26 of the driver-extractor and is threaded onto boss 30. Because of the length of portion 26, the cannula is thereby removed from the patient. The weighted member 38 then is slid along cylindrical portion 32 of the driver-extractor so as to repeatedly impact the annular stop element 36. The force imparted to element 36 is translated by portion 26 of the driver-extractor 24 to drive the staple 40 into the bone. When the staple is fully driven home, the driver-extractor is unscrewed from the staple and is withdrawn from the patient.

To remove the staple, the cannula again is inserted in the patient in the same manner previously described, and the projection 28 of the driver-extractor is screwed into aperture 56 of the staple. The cannula then is withdrawn and secured to boss 30 while the weighted member 38 is repeatedly impacted against stop member 34 to remove the staple from the bone. Thereafter, the cannula is reinserted to guide the staple and the driver-extractor as they are withdrawn from the patient.

The various elements of the fixation system which have been described preferably are made of corrosion-resistant, stainless steel. Additionally, this steel is magnetic so as to facilitate the manipulation or retrieval of parts, if this becomes necessary.

What is claimed is:

1. An arthroscopic ligamentous and capsular fixation system, comprising:
    a substantially cylindrical cannula having a hollowed interior and provided with a threaded portion at one end thereof;
    a driver-extractor device, said device including:
    (a) a first portion dimensioned to be received within the hollowed interior of said cannula and having a length greater than that of the cannula;
    (b) a second portion axially aligned with the first portion and having stop elements at its ends;
    (c) a movable member slidable along said second portion between said stop elements; and
    (d) a threaded portion located at an end of said first portion adjacent one of said stop elements, said threaded portion being dimensioned to cooperate with the threaded portion of the cannula to thereby permit the cannula to be selectively secured in fixed relationship to the driver-extractor device;
    a surgical staple having a generally circular cross-section dimensioned to permit said staple to be received within, and to be slidable along, the hollowed interior of the cannula; and
    means for removably securing said staple to the first portion of the driver-extractor device at the end thereof opposite that at which the threaded portion is located.

2. A system according to claim 1, wherein the cannula is provided with a knob at said one end thereof; and wherein the threaded portion of the cannula is an interiorly threaded passage within said knob axially aligned with the longitudinal axis of the cannula.

3. A system according to claim 2, wherein the threaded portion of said driver-extractor device comprises a threaded boss adapted to be received within the threaded passage in the knob of the cannula.

4. A system according to claim 1, wherein said staple further comprises a cylindrical base from which a pair of tapered legs project, said legs having outer surfaces generally corresponding to the curvature of the base and being serrated along their edges to form a series of teeth.

5. A system according to claim 4, wherein each of said teeth is inclined at an engle of approximately 18° to the longitudinal axis of the staple; and wherein the legs terminate in square-ended tips, at least one of the inner and outer surfaces of the tips being sloped at an angle of approximately 5° to the longitudinal axis of the respective leg.

6. A system according to claim 4, wherein said legs meet the base at generally U-shaped intersections.

7. A system according to claim 4, wherein said means for removably securing said staple to the first portion of the driver-extractor device comprises a threaded projection extending from said opposite end of the first portion, said projection being dimensioned to cooperate with an interiorly threaded aperture provided in the base of said staple.

8. A system according to claim 7, wherein said legs of the staple meet the base at generally U-shaped intersections and terminate in square-ended tips, at least one of the inner and outer surfaces of the tips being sloped at an angle of approximately 5° to the longitudinal axis of the respective leg; and wherein each of said teeth on the legs is inclined at an angle of approximately 18° to the longitudinal axis of the staple.

9. A system according to claim 8, wherein the cannula is provided with a knob at said one end thereof; and wherein the threaded portion of the cannula is an interiorly threaded passage within said knob axially aligned with the longitudinal axis of the cannula.

10. A system according to claim 9, wherein the threaded portion of said driver-extractor device comprises a threaded boss adapted to be received within the threaded passage in the knob of the cannula.

* * * * *